US012569415B2

(12) United States Patent (10) Patent No.: US 12,569,415 B2

Kawaguchi et al. (45) Date of Patent: Mar. 10, 2026

---

(54) GEL-TYPE COSMETIC

(71) Applicant: Shiseido Company, Ltd., Tokyo (JP)

(72) Inventors: Tatsuya Kawaguchi, Tokyo (JP);
Shinichiro Nakano, Tokyo (JP)

(73) Assignee: Shiseido Company, Ltd., Tokyo (JP)

( * ) Notice: Subject to any disclaimer, the term of this
patent is extended or adjusted under 35
U.S.C. 154(b) by 842 days.

(21) Appl. No.: 17/418,616

(22) PCT Filed: Dec. 27, 2019

(86) PCT No.: PCT/JP2019/051440
§ 371 (c)(1),
(2) Date: Jun. 25, 2021

(87) PCT Pub. No.: WO2020/138424

PCT Pub. Date: Jul. 2, 2020

(65) Prior Publication Data

US 2022/0071859 A1     Mar. 10, 2022

(30) Foreign Application Priority Data

Dec. 28, 2018    (JP) ................................. 2018-248470

(51) Int. Cl.
 *A61K 8/04*       (2006.01)
 *A61K 8/73*       (2006.01)
 *A61K 8/81*       (2006.01)
 *A61Q 19/00*      (2006.01)

(52) U.S. Cl.
 CPC .............. *A61K 8/042* (2013.01); *A61K 8/732*
 (2013.01); *A61K 8/8147* (2013.01); *A61Q*
 *19/00* (2013.01); *A61K 2800/10* (2013.01)

(58) Field of Classification Search
 CPC ...... A61K 8/042; A61K 8/732; A61K 8/8147;
      A61K 2800/10; A61Q 19/00
 See application file for complete search history.

(56) References Cited

U.S. PATENT DOCUMENTS

2016/0374933 A1* 12/2016 Tanner ................... A61Q 15/00
                                              424/401

FOREIGN PATENT DOCUMENTS

| EP | 2774598 A1 * | 9/2014 | .............. A61K 8/35 |
|---|---|---|---|
| JP | 2002-047134 A | 2/2002 | |
| JP | 2013-544280 A | 12/2013 | |
| JP | 2014237628 A * | 12/2014 | |
| JP | 2016-027026 A | 2/2016 | |
| JP | 2016-121140 A | 7/2016 | |
| JP | 2017-109962 A | 6/2017 | |
| JP | 2017-214293 A | 12/2017 | |
| JP | 2018-095611 A | 6/2018 | |
| JP | 2018-518516 A | 7/2018 | |
| WO | WO-2014/083116 A2 | 6/2014 | |
| WO | WO-2019/044880 A1 | 3/2019 | |

OTHER PUBLICATIONS

Sodium acrylates crosspolymer-2; https://www.koboproductsinc.com/formulations/KEY-043-EU.pdf (site accessed Mar. 2024) (Year: 2015).*
Machine translation for JP-2014237628-A (Year: 2014).*
Viscosity measurements; https://www.byk-instruments.com/en/t/knowledge/viscometry-measurement (accessed Jan. 2025) (Year: 2025).*
Chemical-Navi, "Aron NT-Z, Water-Absorbent Powder that Creates a Never-Before-Seen Matte Sensation," Jun. 16, 2017, https://www.chemical-navi.com/column/cosmetics/2017-06-16/3417, 2 pages.

* cited by examiner

*Primary Examiner* — Robert A Wax
*Assistant Examiner* — John W Lippert, III
(74) *Attorney, Agent, or Firm* — Foley & Lardner LLP

(57) ABSTRACT

An objective of the present invention is to provide a gel-type cosmetic having a sherbet-like appearance and providing a visually cool impression, wherein the cosmetic can provide a unique texture as of softly bursting and spurting water, while having a smooth texture when applied. The present invention pertains to a gel-type cosmetic containing (A) at least one type of water-absorbing powder having a water absorption factor of 20 to 30 times its own weight; and (B) at least one type of granular water-absorbing polymer having a water absorption factor of at least 100 times its own weight; wherein a total blended amount of the (A) water-absorbing powder and the (B) granular water-absorbing polymer is 1.0% to 4.5% by mass, and the cosmetic has a viscosity of 50,000 to 150,000 mPa·s.

4 Claims, No Drawings

GEL-TYPE COSMETIC

CROSS-REFERENCE TO RELATED APPLICATIONS

This application is the U.S. National Stage of PCT/JP2019/051440 filed Dec. 27, 2019, which claims priority to JP 2018-248470, filed Dec. 28, 2018.

TECHNICAL FIELD

The present invention relates to a gel-type cosmetic having a novel appearance and feeling in use. More specifically, the present invention relates to a gel-type cosmetic having a sherbet-like appearance wherein, when applied to skin, the cosmetic can provide a unique texture as of bursting and spurting water.

BACKGROUND ART

Gel-type cosmetics, particularly aqueous gel cosmetics, are favored for providing a watery texture to skin on which they are applied. While various types of polymer thickeners are blended in order to provide a cosmetic with a gel-type form, there were problems in that, when the blended amounts thereof are increased, there is stickiness and slipperiness during application or after application.

Patent Document 1 discloses a gel-type cosmetic containing sodium polyacrylate starch, and a water-absorbing powder (for example, bentonite, crystalline cellulose, fine-particle silica or the like) that has a maximum wettability of 2 mN or more and that is in a lumpy state at least one point when 1 to 5 ml/g of purified water is added. Said cosmetic is described as achieving an excellent sense of depth and a good moisturizing sensation. However, having an excellent sense of depth refers to the cosmetic having a strong sense of adhesion to the skin and being heavy to spread when applied.

Patent Document 2 discloses a gel-type cosmetic containing a hydrophobically modified polyether urethane such as Adekanol (trade name), sodium polyacrylate starch and a water-swellable clay mineral (for example, bentonite). Said cosmetic is described as having excellent hardness stability and exhibiting good, non-sticky properties in use. However, the cosmetic of Patent Document 2 had a texture in use that was hard in terms of the hardness range.

RELATED ART

Patent Documents

Patent Document 1: JP 2018-95611 A
Patent Document 2: JP 6209386 B

SUMMARY OF THE INVENTION

Problem to be Solved by the Invention

The present invention addresses the problem of providing a gel-type cosmetic having a sherbet-like appearance and thus providing a visually cool impression, wherein the cosmetic provides a unique texture as of softly bursting and spurting water (hereinafter also referred to as a "water-bursting sensation"), while having a smooth texture when applied.

The "sherbet-like appearance" in the present specification refers to an appearance as of sherbet, the food product (frozen confectionery), in other words, an appearance that brings to mind a frosty texture as if a liquid has been frozen and crushed.

Means for Solving the Problem

The present inventors performed diligent research towards solving the aforementioned problem, as a result of which they discovered that the aforementioned unique appearance and feeling in use can be achieved by combining and blending at least one each of a water-absorbing powder having a water absorption factor of 20 to 30 times its own weight and a granular water-absorbing polymer having a water absorption factor of at least 100 times its own weight, and also adjusting the total blended amount of both and the viscosity of the cosmetic to be within specified ranges, thereby completing the present invention.

In other words, the present invention provides a gel-type cosmetic containing (A) at least one type of water-absorbing powder having a water absorption factor of 20 to 30 times its own weight; and (B) at least one type of granular water-absorbing polymer having a water absorption factor of at least 100 times its own weight; wherein a total blended amount of the (A) water-absorbing powder and the (B) granular water-absorbing polymer is 1.0% to 4.5% by mass, and the cosmetic has a viscosity of 50,000 to 150,000 mPa·s.

Effects of the Invention

The gel-type cosmetic of the present invention contains suitable amounts of a water-absorbing powder and a granular water-absorbing polymer, which appropriately absorb water and form gel-type structures, thereby exhibiting a sherbet-like appearance having a viscosity within a prescribed range. For this reason, the gel-type cosmetic of the present invention provides a visually cool impression, while the actual texture is soft to the touch. The gel-type cosmetic of the present invention, when applied to skin, is light and has good spreadability, lacks stickiness or slipperiness, and provides a feeling in use as of bursting and spurting water. After application, a uniform film is formed, with no makeup patchiness or crumbling.

In the present specification, "makeup patchiness" refers to makeup settling in wrinkles and fine lines over time, thereby making the wrinkles more conspicuous. "Crumbling" refers to matter similar to eraser rubbings typically being formed when rubbing skin to which a cosmetic containing a relatively large amount of powder or polymer components has been applied.

MODES FOR CARRYING OUT THE INVENTION

The gel-type cosmetic (hereinafter also referred to simply as "cosmetic") of the present invention contains, as essential ingredients, (A) a water-absorbing powder having a water absorption factor of 20 to 30 times its own weight, and (B) a granular water-absorbing polymer having a water absorption factor of at least 100 times its own weight.

In the present specification, "water absorption factor" is a numerical value indicating the weight of water that can be absorbed by a resin powder in terms of a multiple of the weight of that resin powder itself, as measured by using various measurement methods (for example, a dry weighing method) that are applicable to highly absorbent resin powders. The respective components will be explained in detail below.

(A) Water-Absorbing Powder Having a Water Absorption Factor of 20 to 30 Times its Own Weight The (A) water-absorbing powder having a water absorption factor of 20 to 30 times its own weight (hereinafter referred to as "water-absorbing powder" or "component (A)") in the cosmetic of the present invention is a powder component that can absorb water in an amount that is 20 to 30 times the dry weight of the powder, wherein each powder particle swells by absorbing water but retains the particulate shape. The particle size of the (A) powder particles is not particularly limited. However, particles having a particles size of 1 to 50 μm, preferably 1 to 30 μm, are normally used. The (A) water-absorbing powder may be blended as one type or as a mixture of two or more types.

The (A) water-absorbing powder is preferably a powder comprising a crosslinked acrylic acid polymer. In particular, the powder known by the cosmetic ingredient nomenclature (INCI name) "sodium acrylates crosspolymer-2" is preferred. Powders comprising sodium acrylates crosspolymer-2 are available as commercial products, an example being ARON NT-Z (manufactured by Toagosei). This commercial product is known to have a water absorption factor of approximately 24.

(B) Granular Water-Absorbing Polymer Having a Water Absorption Factor of at Least 100 Times its Own Weight The (B) granular water-absorbing polymer having a water absorption factor of at least 100 times its own weight (hereinafter referred to as the "granular water-absorbing polymer" or "component (B)") in the cosmetic of the present invention is a granular polymer component that can absorb water in an amount that is at least 100 times the dry weight of the powder. The (B) granular water-absorbing polymer is granular (powdered) when dry, but may become deformed by absorbing a large amount of water. The particle size of the (B) granular water-absorbing polymer when dry is not particularly limited.

As the (B) granular water-absorbing polymer, polymer grains having a polyacrylic acid salt structure in the molecule are preferably used. For example, polyacrylic acid salts including crosslinked or non-crosslinked sodium polyacrylate (for example, INCI name: sodium carbomer), polymers having acrylic acid graft-polymerized to a saccharide such as a starch (for example, INCI name: sodium polyacrylate starch) and the like are preferable examples. The (B) granular water-absorbing polymer may be blended as one type or as a mixture of two or more types.

A commercial product may be used as the (B) granular water-absorbing polymer in the present invention. As sodium carbomers, AQUAKEEP (manufactured by Sumitomo Seika Chemicals) and AQUPEC MG N40R (manufactured by Sumitomo Seika Chemicals) are known, and as sodium polyacrylate starches, MAKIMOUSSE 12 (average particle size approximately 12 μm) (manufactured by Daito Kasei Kogyo), MAKIMOUSSE 25 (average particle size approximately 25 μm) (manufactured by Daito Kasei Kogyo) and SANFRESH ST-100 (manufactured by Sanyo Chemical) are known, and may be favorably used in the present invention.

In the cosmetic of the present invention, the total blended amount of the (A) water-absorbing powder and the (B) granular water-absorbing polymer should be 1.0% to 4.5% by mass, preferably 1.5% to 4.5% by mass, and more preferably 2.0% to 4.0% by mass relative to the total amount of the cosmetic. By setting the total blended amount to be within the range from 1.0% to 4.5% by mass, the cosmetic can be prepared so as to be within an appropriate viscosity range for a gel-type cosmetic, and so as to exhibit a sherbet-like appearance and provide a texture as of bursting and spurting water (water-bursting sensation) when applied, with no makeup patchiness or crumbling.

The cosmetic of the present invention has a viscosity that is appropriate for a gel-type cosmetic, the viscosity range thereof being 50,000 to 150,000 mPa·s, preferably 50,000 to 100,000 mPa·s. The viscosity in the present specification refers to the value as measured with a B-type viscometer at 30° C.

The blended amount of the (A) water-absorbing powder in the cosmetic of the present invention need only be such that the total blended amount together with the (B) granular water-absorbing polymer satisfies the aforementioned condition (1.0% to 4.5% by mass), but should normally be 0.5% to 4.0% by mass, preferably 1.0% to 3.8% by mass, and more preferably 2.0% to 3.5% by mass relative to the total amount of the cosmetic. If the blended amount is less than 0.5% by mass, then a water-bursting sensation cannot be obtained, and if the blended amount exceeds 4.0% by mass, then there are cases in which "makeup patchiness" occurs.

The blended amount of the (B) granular water-absorbing polymer in the cosmetic of the present invention need only be such that the total blended amount together with the (A) water-absorbing powder satisfies the aforementioned condition (1.0% to 4.5% by mass), but should normally be 0.1% to 1.0% by mass, preferably 0.2% to 0.8% by mass, and more preferably 0.3% to 0.5% by mass relative to the total amount of the cosmetic. If the blended amount of the (B) granular water-absorbing polymer is less than 0.1% by mass or exceeds 1.0% by mass, then there are cases in which the desired properties cannot be obtained.

In the cosmetic of the present invention, the ratio (mass ratio) of the blended amount of the (B) granular water-absorbing polymer to the blended amount of the (A) water-absorbing powder, in other words, the value [(B)/(A)], is preferably within the range 1/10 to 4/1, and more preferably within the range 1/10 to 2/1.

The cosmetic of the present invention is prepared by dispersing the prescribed amounts of the (A) water-absorbing powder and the (B) granular water-absorbing polymer in water. In other words, the cosmetic of the present invention is a gel-type aqueous cosmetic having a sherbet-like appearance.

The blended amount of water in the cosmetic of the present invention is not particularly limited, but should be at least 60% by mass, preferably at least 70% by mass, and more preferably at least 80% by mass relative to the total amount of the cosmetic.

In the cosmetic of the present invention, one or more (C) oil-absorbing powders may be blended, as appropriate, in addition to the aforementioned essential components (A) and (B), as well as water. By blending a (C) oil-absorbing powder, sebum and oils on the skin to which the cosmetic has been applied can be absorbed, thereby imparting a fresh texture.

The (C) oil-absorbing powder that is preferably used in the cosmetic of the present invention is not particularly limited, but should normally be a powder having an oil absorption capacity of at least 20 ml/100 g, preferably at least 50 ml/100 g, and more preferably at least 80 ml/100 g.

Specific examples of the (C) oil-absorbing powder include silica (porous), methyl methacrylate crosspolymer, calcium carbonate, polymethyl silsesquioxane, nylon, polyurethane, starch, polyethylene, silicone elastomer and the like. In the present invention, a spherical powder having high oil absorption capacity is particularly preferred, and a spherical powder comprising silica and methyl methacrylate crosspolymer can be particularly favorably used.

As the (C) oil-absorbing powder, it is possible to use a type that is commercially available. Examples of silica powders that are commercially available include Sunsphere L-51S (manufactured by AGC Si-Tech) and Silica Micro-beads P-1500 (manufactured by JGC C&C), and examples of methyl methacrylate crosspolymer powders include Microsphere M-100 and M-330 (manufactured by Matsumoto Yushi-Seiyaku).

The blended amount of the (C) oil-absorbing powder in the cosmetic of the present invention should normally be 0.1% to 5.0% by mass, preferably 0.2% to 3.0% by mass, and more preferably 0.5% to 2.0% by mass relative to the total amount of the cosmetic. If the blended amount is less than 0.1% by mass, then the effects of blending the oil-absorbing powder cannot be obtained, and if the blended amount exceeds 5.0% by mass, then there are cases in which squeakiness is exhibited, and makeup patchiness and crumbling may occur.

In the cosmetic of the present invention, other optional components that can be blended into aqueous gel-type cosmetics may be blended, as appropriate, within a range not compromising the effects of the present invention. The other optional components are not limited, but examples include humectants, surfactants, cooling agents, preservatives, chelating agents, fragrances, various types of medicinal agents, stabilizers, masking agents, colorants, essential oils and the like.

Humectants include, for example, 1,3-butylene glycol, polyethylene glycol, propylene glycol, dipropylene glycol (DPG), hexylene glycol, glycerin, diglycerin, xylitol, maltitol, maltose, D-mannitol, trehalose, erythritol, propanediol, glucose, polyoxyethylene methyl glucoside and the like.

As surfactants, non-ionic surfactants such as polyoxyethylene polyoxypropylene alkyl ether can be favorably used.

Examples of cooling agents include 1-menthol and the like.

Chelating agents include, for example, sodium edetic acid salts, sodium metaphosphate, phosphoric acid and the like.

The cosmetic of the present invention may be produced in accordance with a conventionally used method. For example, it may be produced by separately mixing the aqueous components, the powder components and the oil-based components, adding the powder components and the oil-based components to the aqueous components, and stirring.

The cosmetic of the present invention has a sherbet-like appearance that gives an impression of coolness, and provides a texture as of bursting and spurting water when applied. Therefore, it is suitable for providing a skin cosmetic taking advantage of these characteristics such as, for example, a summer skin-care cosmetic or the like.

EXAMPLES

Hereinafter, the present invention will be explained in further detail by providing examples. However, the present invention is not limited by these examples.

The blended amounts, where not noted otherwise, are indicated in percentage by mass relative to the total amount of the cosmetic (sample) in which that component is blended.

Gel-type cosmetics (samples) having the formulations indicated in the tables below were prepared in accordance with conventional methods. Samples of each of the examples were evaluated in accordance with the methods below in the categories below. The results are also indicated in the tables.

(1) Viscosity

After preparing a sample of each example, the viscosity at 30° C. was measured, using a B-type viscometer (Vismetron viscometer manufactured by Shibaura System), using Rotor No. 6, at a rotation speed of 10 rpm, for one minute.

(2) Feeling in Use as of Bursting and Spurting Water (Water-Bursting Sensation)

Samples of each example were actually used by ten expert panelists, who judged whether or not there was a texture as of the cosmetic bursting and spurting water (water-bursting sensation) when applied. The judgment results of the panelists were evaluated in accordance with the criteria below.

(Evaluation Criteria)

A: Eight or more panelists out of the ten replied that there was a "water-bursting sensation".

B: Seven or fewer panelists replied that there was a "water-bursting sensation", and seven or fewer panelists replied that there was no "water-bursting sensation".

C: Eight or more panelists out of the ten replied that there was no "water-bursting sensation".

(3) Overall Evaluation as Gel Cosmetic

The measurement results of the (1) viscosity above were evaluated overall, based on whether the viscosity was within a range (50,000 to 150,000 mPa·s) appropriate for a gel cosmetic (condition 1), and whether the evaluation result for the water-bursting sensation was "A" (condition 2), as follows:

A: Both condition 1 and condition 2 were satisfied.

B: Either condition 1 or condition 2 was satisfied.

C: Neither condition 1 nor condition 2 was satisfied.

(4) Makeup Patchiness and Crumbling

Samples of each example were actually used by ten expert panelists, who visually observed whether or not crumbling occurred when rubbing skin to which the samples were applied. Furthermore, the respective panelists judged, by visual observation, whether or not there was makeup patchiness one hour after applying the cosmetic. The judgment results were evaluated in accordance with the criteria indicated below.

(Evaluation Criteria)

A: Eight or more panelists out of the ten replied that makeup patchiness or crumbling was not observed.

B: Seven or fewer panelists replied that makeup patchiness or crumbling was not observed, and seven or fewer panelists replied that makeup patchiness or crumbling was observed.

C: Eight or more panelists out of the ten replied that makeup patchiness or crumbling was observed.

TABLE 1

| | Comp Ex 1 | Comp Ex 2 | Comp Ex 3 | Ex 1 | Ex 2 | Comp Ex 4 | Comp Ex 5 | Comp Ex 6 |
|---|---|---|---|---|---|---|---|---|
| Water | bal | bal | bal | bal | bal | bal | bal | bal |
| Ethanol | 3 | 3 | 3 | 3 | 3 | 3 | 3 | 3 |
| Glycerin | 1 | 1 | 1 | 1 | 1 | 1 | 1 | 1 |
| DPG | 5 | 5 | 5 | 5 | 5 | 5 | 5 | 5 |
| Sodium acrylates crosspolymer-2 [a] | 3 | 4.5 | 5 | 3 | 3 | 3 | 3 | 3 |
| Sodium carbomer [b] | — | — | — | 0.3 | — | — | — | — |
| Sodium polyacrylate starch [c] | — | — | — | — | 0.3 | — | — | — |
| Carbomer | — | — | — | — | — | 0.3 | — | — |
| (Ammonium acryloyl dimethyl taurate/VP) copolymer | — | — | — | — | — | — | 0.3 | — |
| (Dimethyl acrylamide/sodium acryloyl dimethyl taurate) crosspolymer | — | — | — | — | — | — | — | 0.3 |
| PPG-13 decyl tetradeceth-24 | 0.2 | 0.2 | 0.2 | 0.2 | 0.2 | 0.2 | 0.2 | 0.2 |
| Methylparaben | q.s. | q.s. | q.s. | q.s. | q.s. | q.s. | q.s. | q.s. |
| Phenoxyethanol | q.s. | g.s. | q.s. | q.s. | q.s. | g.s. | q.s. | q.s. |
| Menthol | 0.03 | 0.03 | 0.03 | 0.03 | 0.03 | 0.03 | 0.03 | 0.03 |
| Disodium edetate | q.s. | q.s. | q.s. | q.s. | q.s. | q.s. | q.s. | q.s. |
| Fragrance | q.s. | q.s. | q.s. | q.s. | q.s. | q.s. | q.s. | q.s. |
| Viscosity (mPa · s/30° C.) | × separated | 71000 | more than 150000 | 84200 | 58300 | 51400 | 57200 | 61400 |
| Water-bursting sensation | — | A | A | A | A | C | C | C |
| Overall evaluation as gel-type cosmetic | C | A | B | A | A | B | B | B |
| Makeup patchiness/crumbling | — | C | C | A | A | A | A | A |

[a] ARON NT-Z (manufactured by Toagosei)
[b] AQUPEC MG N40R (manufactured by Sumitomo Seika Chemicals)
[c] MAKIMOUSSE 25 (manufactured by Daito Kasei Kogyo)

As indicated in Table 1, in Comparative Examples 1 to 3, containing only the (A) water-absorbing powder, when the blended amount thereof was 3% by mass, the cosmetic separated into a gelled layer, in which the powder took in water, and free water that was not able to be taken in by the powder (Comparative Example 1). When the blended amount of the water-absorbing powder was increased to 4.5% by mass, a gel was formed and a water-bursting sensation was obtained, but makeup patchiness and crumbling occurred (Comparative Example 2). When the blended amount of the water-absorbing powder was further increased to 5% by mass, the viscosity of the cosmetic became high and exceeded the range appropriate for a gel, and makeup patchiness and crumbling also occurred (Comparative Example 3).

Conversely, in Examples 1 and 2, in which the (A) water-absorbing powder and the (B) granular water-absorbing polymer were combined and blended within a prescribed range (in the examples, a total of 3.3% by mass), gels in appropriate viscosity ranges were obtained, a water-bursting sensation was provided when applied, and makeup patchiness and crumbling did not occur.

In Comparative Examples 4-6, in which the (B) granular water-absorbing polymer in Example 1 or 2 was substituted with the same amount of another water-soluble polymer (with a water absorption factor lower than 100, i.e., 30 to 50 by simple measurement), a gel was formed, but a water-bursting sensation was not obtained when applied.

Next, samples in which the (C) oil-absorbing powder (a spherical powder of porous silica or methyl methacrylate crosspolymer) was blended into the formulation of Example 1 or 2 were evaluated in the same manner as mentioned above. Additionally, the retention of "smoothness (lack of stickiness)" after the samples were applied to the skin was also evaluated by the criteria below. The results are indicated in Tables 2 and 3 below.

(5) Retention of Smoothness (Lack of Stickiness) of Skin

Samples of each example were actually used by ten expert panelists, who checked whether or not the skin on which each sample was applied was sticky three hours after application. The judgment results were evaluated on the basis of the criteria indicated below.

(Evaluation Criteria)

A: Eight or more panelists out of the ten replied that there was no stickiness.

B: Seven or fewer panelists replied that there was no stickiness, and seven or fewer panelists replied that there was stickiness.

C: Eight or more panelists out of the ten replied that there was stickiness.

TABLE 2

| | Ex 3 | Ex 4 | Ex 5 | Ex 6 | Ex 7 | Ref Ex 1 |
|---|---|---|---|---|---|---|
| Water | bal | bal | bal | bal | bal | bal |
| Ethanol | 3 | 3 | 3 | 3 | 3 | 3 |
| Glycerin | 1 | 1 | 1 | 1 | 1 | 1 |
| DPG | 5 | 5 | 5 | 5 | 5 | 5 |
| Sodium acrylates crosspolymer-2 [a] | 3 | 3 | 3 | 3 | 3 | 3 |
| Sodium carbomer [b] | 0.3 | 0.3 | — | — | — | — |
| Sodium polyacrylate starch [c] | — | — | 0.3 | 0.3 | 0.3 | 0.3 |

TABLE 2-continued

|  | Ex 3 | Ex 4 | Ex 5 | Ex 6 | Ex 7 | Ref Ex 1 |
|---|---|---|---|---|---|---|
| PPG-13 decyl tetradeceth-24 | 0.2 | 0.2 | 0.2 | 0.2 | 0.2 | 0.2 |
| Silica [d] | 0.5 | 1 | 0.5 | 1 | 1.5 | 2 |
| Methylparaben | q.s. | q.s. | q.s. | q.s. | q.s. | q.s. |
| Phenoxyethanol | q.s. | q.s. | q.s. | q.s. | q.s. | q.s. |
| Menthol | 0.03 | 0.03 | 0.03 | 0.03 | 0.03 | 0.03 |
| Disodium edetate | q.s. | q.s. | q.s. | q.s. | q.s. | q.s. |
| Fragrance | q.s. | q.s. | q.s. | q.s. | q.s. | q.s. |
| Overall evaluation as gel-type cosmetic | A | A | A | A | A | A |
| Occurrence of makeup patchiness/crumbling | A | A | A | A | A | C |
| Retention of smoothness | A | A | A | A | A | A |

[a] ARON NT-Z (manufactured by Toagosei)
[b] AQUPEC MG N40R (manufactured by Sumitomo Seika Chemicals)
[c] MAKIMOUSSE 25 (manufactured by Daito Kasei Kogyo)
[d] SUNSPHERE L-51S (manufactured by AGC Si-Tech (formerly Asahi Glass))

TABLE 3

|  | Ex 8 | Ex 9 | Ex 10 | Ex 11 |
|---|---|---|---|---|
| Water | bal | bal | bal | bal |
| Ethanol | 3 | 3 | 3 | 3 |
| Glycerin | 1 | 1 | 1 | 1 |
| DPG | 5 | 5 | 5 | 5 |
| Sodium acrylates crosspolymer-2 [a] | 3 | 3 | 3 | 3 |
| Sodium polyacrylate starch [c] | 0.3 | 0.3 | 0.3 | 0.3 |
| PPG-13 decyl tetradeceth-24 | 0.2 | 0.2 | 0.2 | 0.2 |
| Methyl methacrylate crosspolymer | 0.5 | 1 | 1.5 | 2 |
| Methylparaben | q.s. | q.s. | q.s. | q.s. |
| Phenoxyethanol | q.s. | q.s. | q.s. | q.s. |
| Menthol | 0.03 | 0.03 | 0.03 | 0.03 |
| Disodium edetate | q.s. | q.s. | q.s. | q.s. |
| Fragrance | q.s. | q.s. | q.s. | q.s. |
| Overall evaluation as gel-type cosmetic | A | A | A | A |
| Occurrence of makeup patchiness/crumbling | A | A | A | A |
| Retention of smoothness | A | A | A | A |

[a] ARON NT-Z (manufactured by Toagosei)
[c] MAKIMOUSSE 25 (manufactured by Daito Kasei Kogyo)

As indicated in Tables 2 and 3, even when the (C) oil-absorbing powder was blended, an appropriate viscosity and water-bursting sensation, as prepared by providing a prescribed amount of (A) water-absorbing powder and (B) granular water-absorbing polymer, was maintained. In addition thereto, a "smooth (non-sticky) texture" was imparted by blending the (C) oil-absorbing powder, and this texture was retained for a long time. However, depending on the material of the (C) oil-absorbing powder, crumbling did occur even when the blended amount was 5% by mass or less (Reference Example 1). Therefore, when blending porous silica, the blended amount thereof should preferably be less than 2.0% by mass.

The invention claimed is:

1. A gel cosmetic comprising:

(A) 1.0 to 3.8% by mass of a water-absorbing powder consisting of sodium acrylate crosspolymer-2 and having a water absorption factor of 20 to 30 times its own weight; and (B) 0.2 to 0.8% by mass of granular water-absorbing polymer consisting of sodium polyacrylate starch or sodium carbomer and having a water absorption factor of at least 100 times its own weight; wherein the amount of water is 80% by mass or more; and a total amount of the (A) water-absorbing powder and the (B) granular water-absorbing polymer is 1.5% to 4.5% by mass, and the cosmetic has a viscosity of 50,000 to 84,200 mPa·s measured with a B-type viscometer at 30° C. at a rotation speed of 10 rpm.

2. The gel cosmetic according to claim 1, wherein a ratio [(B)/(A)] of the amount of the (A) water-absorbing powder to the amount of the (B) granular water-absorbing polymer is within a range from 1/10 to 4/1.

3. The gel cosmetic according to claim 1, further comprising (C) an oil-absorbing powder.

4. The gel cosmetic according to claim 3, wherein the (C) oil-absorbing powder is at least one type selected from the group consisting of porous silica, methyl methacrylate crosspolymer, calcium carbonate, polymethyl silsesquioxane, nylon, polyurethane, starch, polyethylene, silicone elastomer and mixtures thereof.

* * * * *